United States Patent
Shi (10) Patent No.: US 9,839,442 B2
(45) Date of Patent: *Dec. 12, 2017

(54) SAFETY SCALPEL (71) Applicant: STERILANCE MEDICAL (SUZHOU) INC., Suzhou, Jiangsu (CN)

(72) Inventor: Guoping Shi, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 235 days.

This patent is subject to a terminal disclaimer.

(21) Appl. No.: 14/421,352

(22) PCT Filed: Sep. 3, 2013

(86) PCT No.: PCT/CN2013/082847
§ 371 (c)(1),
(2) Date: Feb. 12, 2015

(87) PCT Pub. No.: WO2014/036926
PCT Pub. Date: Mar. 13, 2014

(65) Prior Publication Data
US 2015/0182247 A1 Jul. 2, 2015

(30) Foreign Application Priority Data

Sep. 5, 2012 (CN) .......................... 2012 1 0325282

(51) Int. Cl.
*A61B 17/3213* (2006.01)
*A61B 17/3217* (2006.01)
A61B 17/3211 (2006.01)

(52) U.S. Cl.
CPC ...... *A61B 17/3213* (2013.01); *A61B 17/3217* (2013.01); *A61B 2017/32113* (2013.01)

(58) Field of Classification Search
CPC ........... A61B 2017/32113; A61B 2017/32116; A61B 17/3211; B26B 1/00; B26B 1/10;
(Continued)

(56) References Cited

U.S. PATENT DOCUMENTS 3,793,726 A * 2/1974 Schrank ............ A61B 17/3215
30/151
3,905,101 A * 9/1975 Shepherd ........... A61B 17/3213
30/162
(Continued)

FOREIGN PATENT DOCUMENTS

CN 2621611 Y 6/2004
CN 101642383 A 2/2010
(Continued)

OTHER PUBLICATIONS

Nov. 28, 2013 International Search Report issued in International Application No. PCT/CN2013/082847.

Primary Examiner — Jason Daniel Prone
Assistant Examiner — Richard Crosby, Jr.
(74) Attorney, Agent, or Firm — Oliff PLC (57) ABSTRACT A safety scalpel is made of a blade shield, blade, blade holder and handle. The blade holder is located in the front portion of the handle and the blade holder and handle are of integral connection structure or separate plug type connection structure. The blade is fixed in the front portion of the blade holder and the blade shield is slidably mounted on the blade holder, wherein: the blade holder is provided with a first sliding channel and the first sliding channel is provided with a first front locking channel at its front end. A deadlock channel is set in front of the first front locking channel. The blade shield may be moved further forward after use to make the first protrusion of blade shield fall in deadlock channel to enter the deadlocking state. The construction thoroughly eliminates the safety problem of reusing scalpel.

7 Claims, 6 Drawing Sheets (58) Field of Classification Search
CPC .......... B26B 5/00–5/008; Y10T 103/16; Y10T 103/1608; Y10T 103/1616; Y10T 103/1624; Y10T 103/1666; Y10T 103/1674
USPC .......................... 30/151, 162; 606/166, 167
See application file for complete search history.

(56) References Cited

U.S. PATENT DOCUMENTS

| | | | |
|---|---|---|---|
| 3,906,626 A * | 9/1975 | Riuli | A61B 17/3213 30/162 |
| 6,626,925 B2 | 9/2003 | Newman et al. | |
| D482,788 S * | 11/2003 | Montgomery | D24/128 |
| 7,087,067 B2 | 8/2006 | Kehr et al. | |
| 7,346,989 B2 | 3/2008 | Shi | |
| 9,113,946 B2 * | 8/2015 | Hajgato | A61B 17/3213 |
| 9,636,141 B2 * | 5/2017 | Shi | A61B 17/3213 |
| 9,693,797 B2 * | 7/2017 | Austria | A61B 17/3213 |
| 2004/0098001 A1 * | 5/2004 | Holman | A61B 17/3213 606/167 |
| 2004/0181247 A1 | 9/2004 | Kehr et al. | |
| 2004/0236359 A1 | 11/2004 | Shi | |
| 2005/0203555 A1 | 9/2005 | Griffin et al. | |
| 2006/0212058 A1 | 9/2006 | Djordjevic et al. | |

FOREIGN PATENT DOCUMENTS

| | | | |
|---|---|---|---|
| CN | 102835991 A | 12/2012 | |
| CN | 102835992 A | 12/2012 | |
| CN | 102871706 A | 1/2013 | |
| EP | 0988832 A2 | 3/2000 | |

* cited by examiner

SAFETY SCALPEL

TECHNICAL FIELD

The present invention relates to a medical surgical scalpel, particularly to a kind of shielded safety scalpel. The shield can be pushed to a deadlocking state, so that the shield cannot be reused after the use of scalpel.

BACKGROUND OF INVENTION

The scalpel is a necessary tool for surgical operation and its safety is extremely important to healthcare workers and patients. A conventional scalpel usually consists of two types: one type is a plastic handled scalpel and the other is steel handled scalpel. The plastic handled scalpel mainly consists of a disposable blade and disposable plastic handle. The plastic handle is provided with a blade holder at its front part and the blade is installed on the blade holder. The steel handled scalpel mainly consists of a disposable blade and reusable steel handle and it's necessary to install the blade onto the handle before use and remove the blade from handle after use. Whether the plastic handled scalpel or steel handled scalpel, the user is subject to the potential injury caused by an exposed or contaminated blade during normal use of the instrument, or when passing the exposed scalpel to the colleague.

In order to improve safety, existing surgical scalpels have been designed incorporating the concept of carrying a shield. For example, U.S. Pat. No. 6,626,925B2 discloses an invention patent application titled Shielded Surgical Scalpel applied by American BD Company (Becton, Dickinson Company), which belongs to a shielded plastic handled surgical scalpel. Also, for example, European patent EP0988832A2 discloses an invention patent application titled Surgical Scalpel applied by American BD Company (Becton, Dickinson Company), which belongs to a shielded steel handled scalpel. Although this kind of sliding sleeve type surgical scalpel applying the shield structure solves the safety problem caused by the exposed blade, it has not fundamentally solved the safety problem of potential re-use of the scalpel, since it remains possible to open the shield after the open and closing sequence of normal use.

Therefore, it's urgently necessary to invent a kind of safe and reliable scalpel, which could overcome the above described disadvantages of scalpels in prior art and serve the medical care industry better.

DISCLOSURE OF THE INVENTION

In view of the above described disadvantages of scalpels in prior art, the present invention is devised to provide a kind of safety scalpel to solve the safety problem of reusing the scalpels in prior art.

In order to achieve the above object, the present invention provides the technical solution: a kind of safety scalpel, which consists of a blade shield, blade, blade holder and handle. The blade holder is located in a front portion of the handle and the blade holder and handle are of an integral connection structure or separate plug-together type connection structure. The blade is fixed in the front portion of the blade holder and the blade shield is slidably mounted on the blade holder, wherein:

The said blade shield is provided with one top unlocking button, which is a first flexible cantilever structure on the blade shield. The first flexible cantilever is provided with a second locking protrusion, which includes a first protrusion; the blade holder is provided with a first sliding channel for the first protrusion correspondingly, and the first sliding channel is arranged along the blade holder with respect to the sliding direction of the blade shield. The first sliding channel is provided with a first front locking channel at its front end and the first front locking channel is connected with front end of first sliding channel. A deadlock channel is set in front of the first front locking channel and a locking block is set between the deadlock channel and the first front locking channel;

During the operation process of the scalpel, the first protrusion forms the following different states when it mates with the first front locking channel, first sliding channel and deadlock channel respectively:

a. When the first protrusion is located in the first front locking channel, the blade is arranged inside the blade shield and the blade holder and blade are in a locking state with respect to the blade shield;

b. When the top unlocking button is pressed, the top unlocking button forces the first protrusion to move from the first front locking channel to the first sliding channel and in such a state, the blade shield is allowed to move with respect to the blade holder and blade;

c. When the first protrusion travels from the first front locking channel across the locking block to fall into the deadlock channel, the blade is arranged inside the blade shield and the blade holder and blade are in a deadlocking state with respect to the blade shield;

The above described technical solution is explained as follows:

1. In the present invention, the "front" in said "front portion" and "front end" means the direction in which the blade tip points to with respect to the scalpel. The "rear" in said "rear portion" and "rear end" means the direction opposite to the "front".

2. In the above described solution, the said "locking state" means the temporary locking state of the blade holder and blade with respect to the blade shield and the locking state can be released by pressing the top unlocking button. The said "deadlocking state" is different from the locking state. The deadlocking state means the state of permanently locking the blade holder and blade with respect to the blade shield. The deadlocking state is a permanent position and can only be released by wilful damage or misuse.

3. In the above described technical solution, in order to make the blade holder and blade shield smoothly transit from the locking state to the deadlocking state, the side of said locking block adjacent to the first front locking channel is an inclined surface and the side of the locking block adjacent to the deadlock channel is a vertical surface.

4. The technical solution of the present invention includes two types of integral connection of the blade holder and handle and plug-together type connection of blade holder and handle.

When the blade holder and handle are of a plug-together type connection structure, the safety scalpel has the following changes:

(1) In order to further improve the safety of the scalpel, the said blade holder is provided with a flexible arm at the rear end which extends backward. The flexible arm is provided with a locking block and a protrusion block. The protrusion block extends toward the inner wall of the blade shield; and the inner wall of the blade shield is provided with a clearance opening for said protrusion block and the said locking block is provided with a second inclined block in the front portion of the handle; under the initial state (the final assembly state during fabrication), the first protrusion is located in first front locking channel and the protrusion block faces the clearance opening. When the handle is inserted into the blade holder for connection, the second inclined block acts on the locking block to force the flexible arm to be flexed and force the protrusion block to extend into the clearance opening with sideward movement. After the second inclined block travels across the locking block, the flexible arm automatically returns to its initial position resiliently and the second inclined block engages the locking block to connect the handle and blade holder; during removal of the handle, the second inclined block draws the blade holder backward with respect to the blade shield through the locking block to force the first protrusion to travel across the locking block to fall into the deadlock channel and force the protrusion block to misalign with the clearance opening. In such a state, the handle cannot be re-inserted into the blade holder for connection as the protrusion block cannot make sideward movement through the clearance opening.

(2) In order to make the blade assembly comprising of the blade, blade holder and blade shield useful as an independent mini-scalpel or when used as handled scalpel after insertion of a handle, the said blade holder is provided with a second flexible cantilever. One side of the second flexible cantilever is provided with a first locking protrusion, lateral unlocking button and first inclined block; the side of the blade shield is provided with a second sliding channel for said lateral unlocking button, so that the lateral unlocking button is located in the second sliding channel. The second sliding channel is provided with a front indent at its front end and with a rear indent at its rear end. The said first locking protrusion mates with the front indent to lock the blade in an open state with respect to the blade shield and the first locking protrusion mates with the rear indent to lock the blade in a closed state with respect to the blade shield. Pressing the lateral unlocking button can release the mating state of the first locking protrusion and front indent or the mating state of the first locking protrusion and rear indent; the said first inclined block is used to mate with a third locking protrusion set at the front end of the handle. When the handle is connected with the blade holder, the third locking protrusion acts on the first inclined block to force the second flexible cantilever to be flexed, so that the first locking protrusion leaves its original position to be unable to engage the front indent or rear indent; when the handle is pulled out, the third locking protrusion is separated from the first inclined block and the second flexible cantilever automatically returns to its initial position resiliently and returns the first locking protrusion to its initial position, so that the first locking protrusion can engage the front indent or rear indent.

(3) In order to effectively control the opening and closing operation of the blade with respect to the blade shield and the locking in an opening or closing state after the blade holder is inserted into the handle, the said handle is provided with the a third sliding channel used to connect to the said first sliding channel. When the handle and blade holder are connected, the third sliding channel and first sliding channel are abutted, so that the first protrusion can slide along the first sliding channel to the third sliding channel. The said third sliding channel is provided with a first rear locking channel at its rear end and the first rear locking channel is connected with the rear end of the third sliding channel. When the first protrusion is located in the first rear locking channel, the blade extends out of the blade shield and the blade holder and blade are in a locking state with respect to the blade shield.

Furthermore, the said first sliding channel and first front locking channel are set on one lateral face of the blade holder, the said third sliding channel and first rear locking channel are set on one lateral face of the handle, and the fourth sliding channel is set on the opposite lateral face of the handle at the corresponding position to the first sliding channel and third sliding channel. The fourth sliding channel is provided with a second front locking channel at its front end, which is connected with the front end of the fourth sliding channel and the fourth sliding channel is provided with a second rear locking channel at its rear end, which is connected with the rear end of the fourth sliding channel. The positions of the second front locking channel and first front locking channel are corresponding and the positions of the second rear locking channel and first rear locking channel are corresponding; the second locking protrusion includes a second protrusion, which works with the fourth sliding channel, second front locking channel and second rear locking channel.

(4) In order to ensure more reliable connection of the blade holder and handle, the blade holder can be provided with one upper protrusion and the said handle is provided with a lower indent used to work with said upper protrusion. When the handle and blade holder are connected, the said lower indent engages the upper protrusion.

(5) In order to ensure the smooth sliding of the blade holder and handle inside the blade shield, the said blade shield is provided with a protruding rib along the blade holder with respect to the sliding direction of the blade shield, and the blade holder is provided with a fifth sliding channel for said protruding rib. The matching of fifth sliding channel and protruding rib provides for the sliding connection of the blade holder inside the blade shield; the said handle is provided with a sixth sliding channel for said protruding rib and when the handle is inserted into the blade holder, the matching of the sixth sliding channel and protruding rib provides for the sliding connection of the handle inside the blade shield.

When the blade holder and handle are of integral connection structure, the safety scalpel has the following changes:

(1) In order to effectively control the opening and closing operation of the blade with respect to the blade shield and the locking in an opening or closing state, the first sliding channel of said blade holder extends backward along the length of the handle. The first sliding channel is provided with a first rear locking channel at its rear end and the first rear locking channel is connected with the rear end of the first sliding channel. When the first protrusion is located in the first rear locking channel, the blade extends out of the blade shield and the blade holder and blade are in a locking state with respect to the blade shield.

(2) On the basis of the above described (1), the first sliding channel, first front locking channel and first rear locking channel are set on one lateral face of the blade holder and handle, and the fourth sliding channel is set on the opposite lateral face of the blade holder and handle at the corresponding position to the first sliding channel. The fourth sliding channel is provided with a second front locking channel at its front end, which is connected with the front end of a fourth sliding channel and the fourth sliding channel is provided with a second rear locking channel at its rear end, which is connected with the rear end of the fourth sliding channel. The positions of the second front locking channel and first front locking channel are corresponding and the positions of the second rear locking channel and first rear locking channel are corresponding; the said fourth sliding channel, second front locking channel and second rear locking channel are used to work with the second protrusion of the second locking protrusion on the blade shield.

The particular design concept and operating principle of the present invention is: the technical solution of the present invention includes two situations of an integral connection structure of the blade holder and handle and a plug-together type connection structure of the blade holder and handle. In order to thoroughly solve the safety problem of reusing these two kinds of scalpels, a deadlock channel of the present invention is set in front of the first front locking channel and the locking block is set between the deadlock channel and the first front locking channel. After the scalpel is used, pushing or pulling the blade shield further forward makes the first protrusion travel from the first front locking channel across the locking block to fall into the deadlock channel, and the blade is arranged inside the blade shield and the blade holder and blade are thus in a deadlocking state with respect to the blade shield, so that the blade cannot be reused; As the blade holder and blade are permanently locked with respect to the blade shield in the deadlocking state to disable the original function, the safety problem of reusing a scalpel is eliminated.

Additionally, for the scalpel with a plug-together type connection structure of the blade holder and handle, besides the above described pushing or pulling the blade shield further forward to make the scalpel enter a deadlocking state, the removal of the handle after the scalpel is used can make the second inclined block on the handle draw the blade holder backward with respect to the blade shield through locking block to force the first protrusion to travel across the locking block to fall into the deadlock channel to thus be in a deadlocking state, so that it cannot be reused.

For the scalpel with a plug-together type connection structure of the blade holder and handle, the present invention describes another kind of special safety structure, i.e. after removal of the handle, the handle cannot be re-inserted into the blade holder for connection. Particularly: the blade holder of the present invention is provided with a flexible arm at the rear end which extends backward. The flexible arm is provided with a protrusion block at the end of the flexible arm. The inner wall of the blade shield is provided with a clearance opening for said protrusion block. In the initial state, the protrusion block faces the clearance opening. When the handle is inserted to be connected with the blade holder, the flexible arm is flexed and forces the protrusion block to extend into the clearance opening with sideward movement, so that the blade and the blade holder are connected. During removal of the handle, the handle draws the blade holder backward with respect to the blade shield to force the protrusion block to misalign with the clearance opening. In such a state, the handle cannot be inserted to be connected with the blade holder as the protrusion block cannot make sideward movement through the clearance opening. Thus the possibility of reusing the combination of blade holder and handle is eliminated to achieve the safety object of the invention.

The number description of above described drawings is as follows:

1. blade holder; 10. fifth sliding channel; 11. first front locking channel; 12. first sliding channel; 13. first locking protrusion; 14. lateral unlocking button; 140. second flexible cantilever; 15. first inclined block; 16. locking block; 17. flexible arm; 171. locking block; 172. protrusion block; 18. upper protrusion; 19. deadlock channel;
2. blade;
3. blade shield; 31. top unlocking button; 32. second locking protrusion; 321. first protrusion; 322. second protrusion; 33. second sliding channel; 34. front indent; 35. rear indent; 36. protruding rib; 37. clearance opening; 38. window;
4. handle; 41. third sliding channel; 42. first rear locking channel; 43. fourth sliding channel; 44. second inclined block; 45. lower indent; 46. third locking protrusion; 47. second front locking channel; 48. second rear locking channel; 49. sixth sliding channel.

SPECIFIC EMBODIMENT

With reference to the accompanying drawings and embodiment, the present invention will be described in detail.

Embodiment 1

Figure 1:
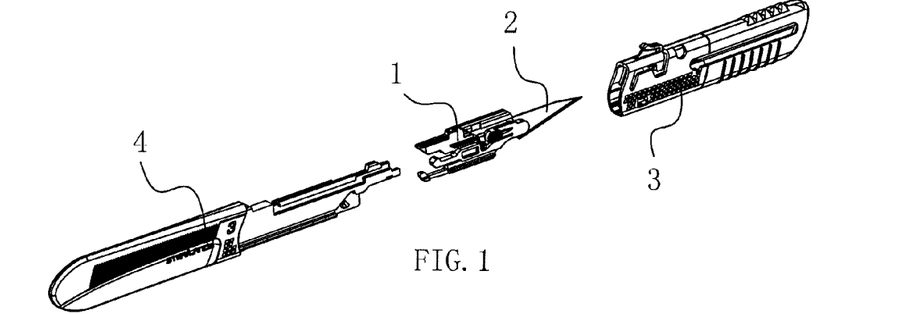
FIG. 1 is the exploded perspective view of safety scalpel of embodiment 1 of the present invention.

A Kind of Safety Scalpel with a Separate Plug-Together Type Connection Structure of the Blade Holder and Handle Refer to FIG. 1. The safety scalpel consists of a disposable blade assembly and reusable handle 4, wherein the said blade assembly consists of blade 2, blade holder 1 and blade shield 3. The blade 2 is fixed in the front portion of blade holder 1 and blade shield 3 is slidably mounted onto blade holder 1 and the blade holder 1 is located in the front portion of handle 4 and the blade holder 1 and handle 4 are of the separate plug-together type connection structure. Reusable means it may be used repeatedly. The said handle 4 is a reusable component and it could be made of metal or nonmetal material. A handle 4 made of metal material is more popular with doctors, as it's heavier and it has high strength and good "feel".

The following is detailed description of blade shield 3, blade holder 1 and handle 4.

Refer to FIGS. 2 to 11. The blade assembly consists of blade 2 (see FIG. 2), blade holder 1 (see FIGS. 2 and 4) and blade shield 3 (see FIGS. 5 and 6). The blade 2 is fixed in the front portion of blade holder 1 and blade shield 3 is slidably mounted onto blade holder 1.

Figure 4:
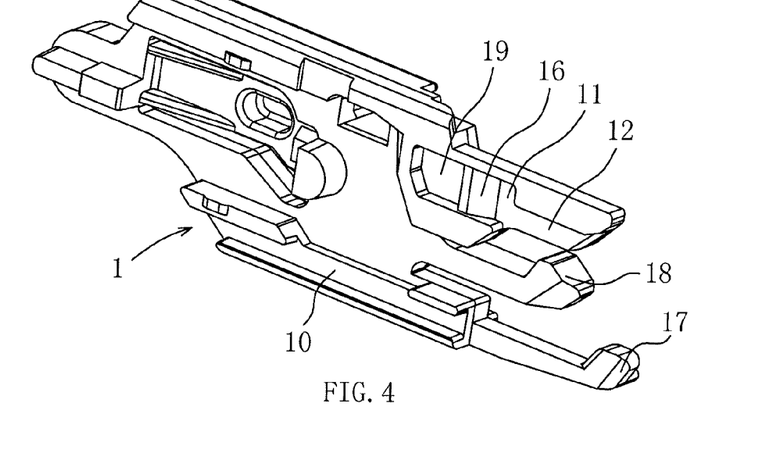
FIG. 4 is the back view illustrating the blade holder of safety scalpel of embodiment 1 of the present invention.
Figure 5:
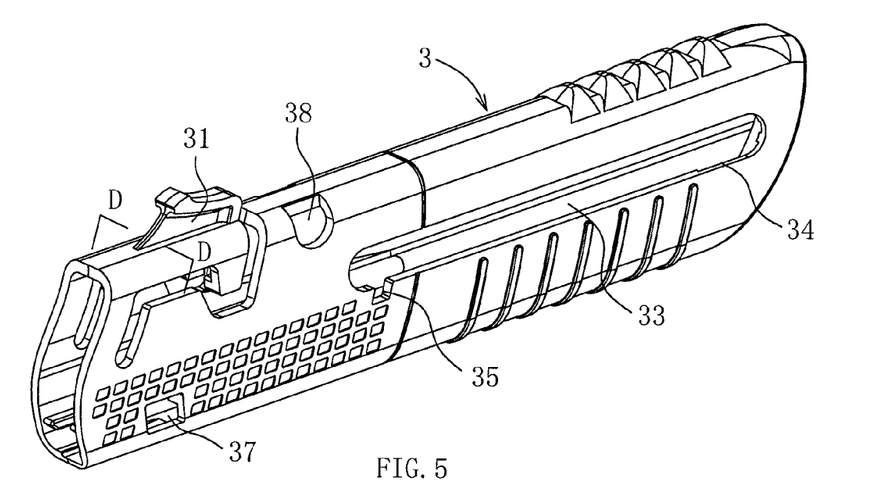
FIG. 5 is the front view illustrating the blade shield of safety scalpel of embodiment 1 and embodiment 2 of the present invention.
Figure 6:
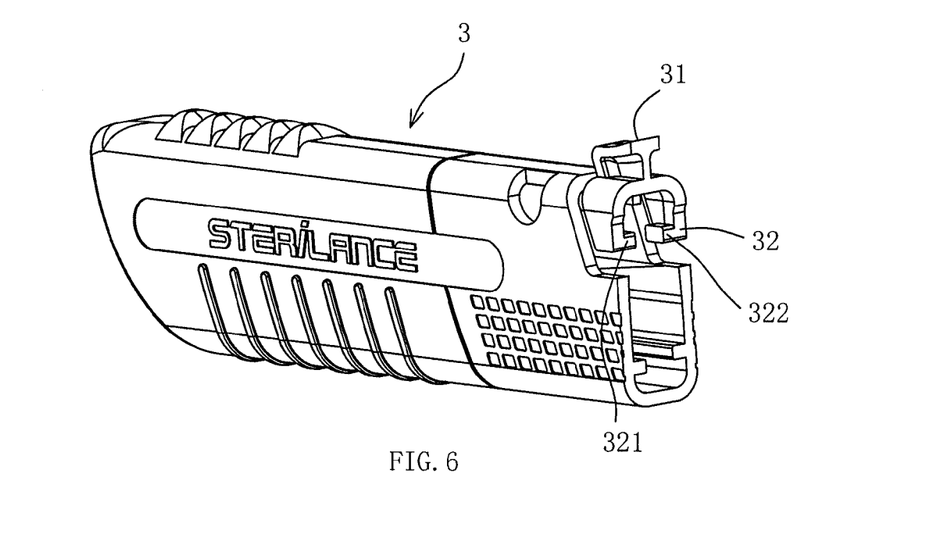
FIG. 6 is the section view along line D-D of FIG. 5.
Figure 7:
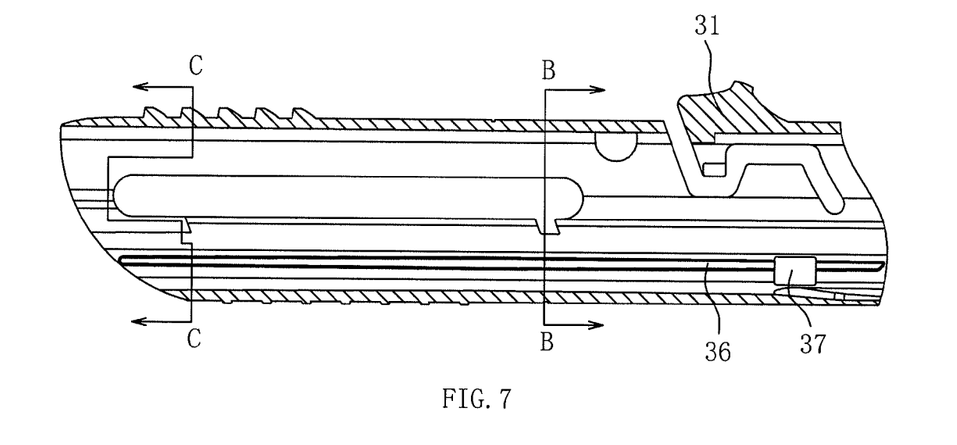
FIG. 7 is the main section view of FIG. 5.
Figure 8:
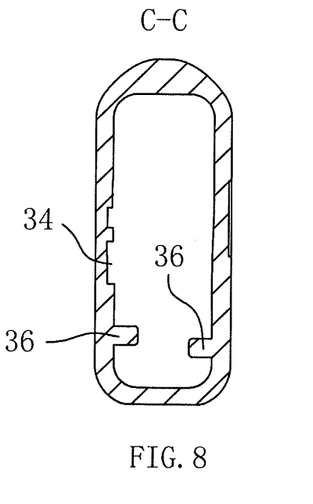
FIG. 8 is the section view along line C-C of FIG. 7.
Figure 9:
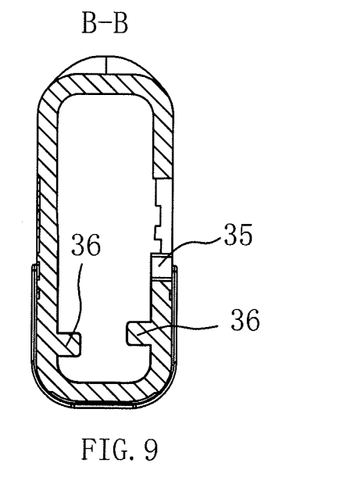
FIG. 9 is the section view along line B-B of FIG. 7.

The said blade shield 3 is provided with one top unlocking button 31 and top unlocking button 31 is a first flexible cantilever structure on the blade shield 3 (see FIGS. 5 and 7). The first flexible cantilever is provided with second locking protrusion 32 (see FIG. 6) and second locking protrusion 32 includes a first protrusion 321. The blade holder 1 is provided with first sliding channel 12 for first protrusion 321 correspondingly (see FIG. 4), and the first sliding channel 12 is arranged along the blade holder 1 with respect to the sliding direction of blade shield 3. The first sliding channel 12 is provided with first front locking channel 11 at its front end and first front locking channel 11 is connected with the front end of first sliding channel 12. A deadlock channel 19 is set in front of first front locking channel 11 (see FIG. 4) and locking block 16 is set between deadlock channel 19 and first front locking channel 11. During the operation process of the scalpel, the first protrusion 321 forms the following different states when it mates with first front locking channel 11, first sliding channel 12 and deadlock channel 19 respectively:

a. When first protrusion 321 is located in first front locking channel 11, the blade 2 is arranged inside blade shield 3 and the blade holder 1 and blade 2 are in a locking state with respect to blade shield 3 and the blade holder 1 and blade 2 are temporarily locked with respect to blade shield 3 in the locking state;

b. When top unlocking button 31 is pressed, top unlocking button 31 forces first protrusion 321 to move from first front locking channel 11 to first sliding channel 12 and in such a state, the blade shield 3 is allowed to move with respect to blade holder 1 and blade 2;

c. When first protrusion 321 travels from first front locking channel 11 across the locking block 16 to fall into the deadlock channel 19, the blade 2 is arranged inside blade shield 3 and the blade holder 1 and blade 2 are in a deadlocking state with respect to blade shield 3 and the deadlocking state can only be released by wilful damage.

Figure 2:
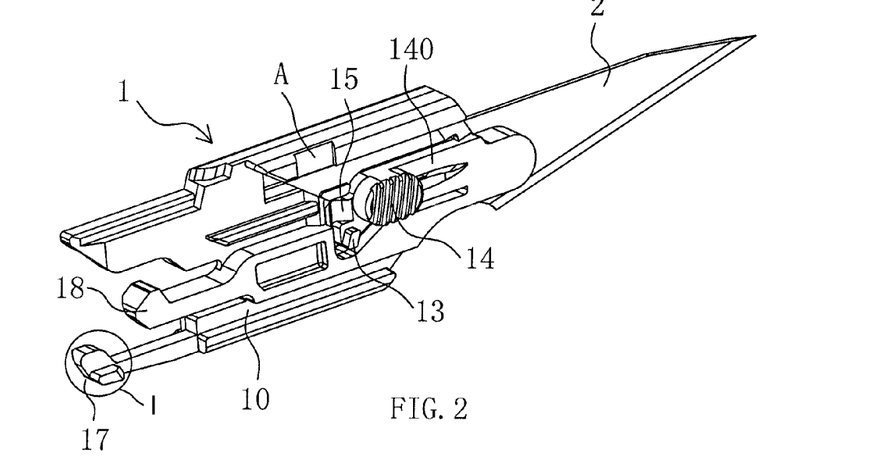
FIG. 2 is the front view illustrating the blade holder and blade of safety scalpel of embodiment 1 of the present invention.
Figure 3:
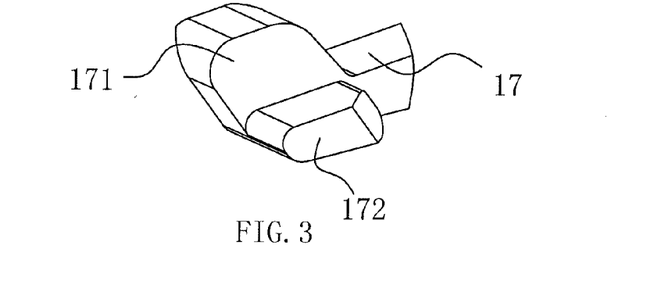
FIG. 3 is the enlarged view of structure I in FIG. 1.

The said blade holder 1 is provided with a flexible arm 17 at its rear end which extends backward (see FIG. 2) and the flexible arm 17 is provided with a locking block 171 and a protrusion block 172 (see FIG. 3). The protrusion block 172 extends towards the inner wall of blade shield 3 in the assembly state. The inner wall of blade shield 3 is provided with a clearance opening 37 for said protrusion block 172 (see FIG. 5) and the handle 4 is provided with second inclined block 44 at its front end for said corresponding locking block 171 (see FIG. 10). In the initial state (the final assembly state of the blade assembly), the first protrusion 321 of said blade assembly is located inside first front locking channel 11 and the protrusion block 172 faces the clearance opening 37. When the handle 4 is inserted into the blade assembly to be connected with blade holder 1, the second inclined block 44 acts on locking block 171 to force the flexible arm 17 to be flexed and force the protrusion block 172 to extend into clearance opening 37 with sideward movement. After the second inclined block 44 travels across the locking block 171, the flexible arm 17 automatically returns to its initial position resiliently and the second inclined block 44 engages the locking block 171 to connect the handle 4 and blade holder 1; During removal of handle 4, the second inclined block 44 draws the blade holder 1 backward with respect to blade shield 3 through locking block 171 to force the first protrusion 321 to travel across locking block 16 to fall in deadlock channel 19 to thus enter a deadlocking state and force the protrusion block 172 to misalign with the clearance opening 37. In such a state, the handle 4 cannot be re-inserted into the blade assembly to be connected with blade holder 1 as the protrusion block 172 cannot make sideward movement through clearance opening 37.

In order to make blade holder 1 and blade shield 3 of the blade assembly smoothly transit from a locking state to a deadlocking state, the side of said locking block 16 adjacent to first front locking channel 11 is an inclined surface and the side of locking block 16 adjacent to deadlock channel 19 is a vertical surface (see FIG. 4).

In order to make the blade assembly useful as a handled scalpel after connection of the blade assembly and handle 4, the said blade holder 1 is provided with second flexible cantilever 140 (see FIG. 2). The second flexible cantilever 140 is provided with first locking protrusion 13, lateral unlocking button 14 and first inclined block 15 on its one side. The blade shield 3 is provided with second sliding channel 33 for said lateral unlocking button 14 on its side (see FIG. 5), so that lateral unlocking button 14 is located in second sliding channel 33. The second sliding channel 33 is provided with front indent 34 at its front end and provided with rear indent 35 at its rear end. The said front indent 34 is a shallow recess in one lateral inner wall of blade shield 3 (see FIG. 8) and the said rear indent 35 is the concave hole connecting the inner wall and outer wall of blade shield 3 (see FIG. 9). The said first locking protrusion 13 mates with front indent 34 to lock the blade 2 in an open state with respect to blade shield 3 and first locking protrusion 13 mates with rear indent 35 to lock the blade 2 in a closed state with respect to blade shield 3. Pressing lateral unlocking button 14 can release the mating state of first locking protrusion 13 and front indent 34 or the mating state of first locking protrusion 13 and rear indent 35.

Figure 10:
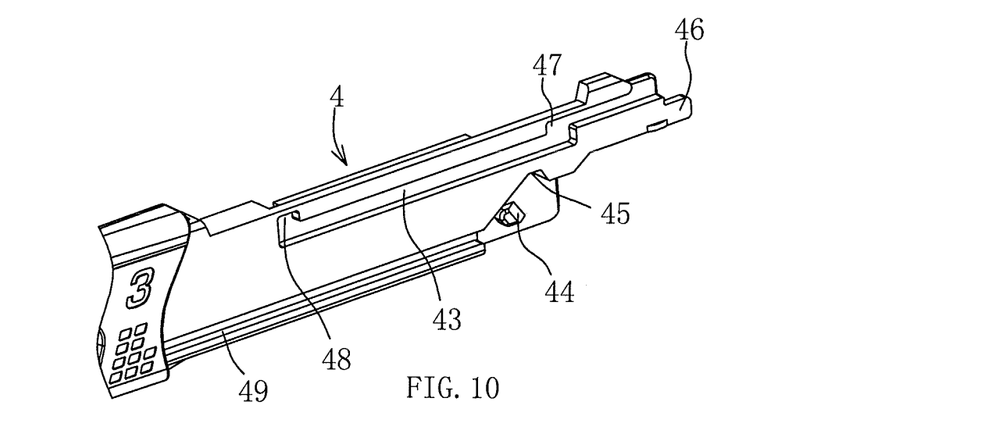
FIG. 10 is the front view illustrating the front end of handle of safety scalpel of embodiment 1 of the present invention.
Figure 11:
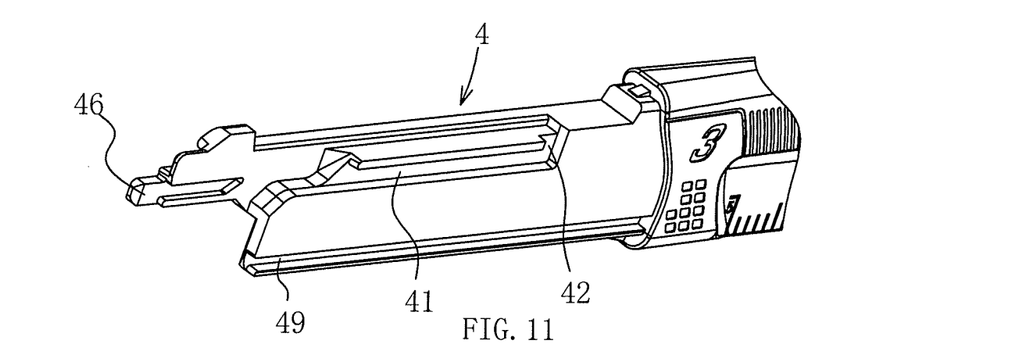
FIG. 11 is the back view illustrating the front end of handle of safety scalpel of embodiment 1 of the present invention.

The said first inclined block 15 (see FIG. 2) on the blade holder 1 is used to mate with third locking protrusion 46 (see. FIG. 10) set at the front end of handle 4. When handle 4 is connected with blade holder 1, the third locking protrusion 46 acts on first inclined block 15 to force second flexible cantilever 140 to be flexed, so that first locking protrusion 13 leaves its original position to be unable to engage front indent 34 or rear indent 35. When the handle 4 is pulled out, the third locking protrusion 46 is separated from first inclined block 15, second flexible cantilever 140 automatically returns to its initial position resiliently and allows the first locking protrusion 13 to return to its initial position, so that first locking protrusion 13 can engage front indent 34 or rear indent 35.

In order to effectively control the opening and closing operation of blade 2 with respect to blade shield 3 and the locking in an opening or closing state after the blade assembly is inserted into handle 4, the said handle 4 is provided with the third sliding channel 41 (see FIG. 11) used to connect the first sliding channel 12 of blade holder 1 (see FIG. 4). When the handle 4 and blade holder 1 are connected, the third sliding channel 41 and first sliding channel 12 are abutted, so that the first protrusion 321 of blade shield 3 can slide along first sliding channel 12 to third sliding channel 41. The said third sliding channel 41 is provided with first rear locking channel 42 at its rear end (see FIG. 11) and the first rear locking channel 42 is connected with the rear end of third sliding channel 41. When first protrusion 321 is located in first rear locking channel 42, the blade 2 extends out of blade shield 3 and blade holder 1 and blade 2 are in a locking state with respect to blade shield 3.

The said first sliding channel 12 and first front locking channel 11 are set on one lateral face of blade holder 1, the said third sliding channel 41 and first rear locking channel 42 are set on one lateral face of handle 4, and fourth sliding channel 43 (see FIG. 10) is set on the opposite lateral face of handle 4 at the corresponding position to first sliding channel 12 and third sliding channel 41. The fourth sliding channel 43 is provided with second front locking channel 47 at its front end, which is connected with the front end of fourth sliding channel 43 and fourth sliding channel 43 is provided with second rear locking channel 48 at its rear end, which is connected with the rear end of fourth sliding channel 43. The positions of second front locking channel 47 and first front locking channel 11 are corresponding and the positions of second rear locking channel 48 and first rear locking channel 42 are corresponding. The second locking protrusion 32 includes second protrusion 322 (see FIG. 6), which is used to work with the fourth sliding channel 43, second front locking channel 47 and second rear locking channel 48.

In order to ensure more reliable connection of blade holder 1 and handle 4, the blade holder 1 is provided with one upper protrusion 18 (see FIGS. 2 and 4) and the said handle 4 is provided with lower indent 45 used to work with said upper protrusion 18 (see FIG. 10). When the handle 4 and blade holder 1 are connected, the said lower indent 45 engages the upper protrusion 18.

In order to ensure the smooth sliding of blade holder 1 and handle 4 inside the blade shield 3, the blade shield 3 is provided with a protruding rib 36 along the blade holder 1 with respect to the sliding direction of blade shield 3 (see FIGS. 8 and 9), and blade holder 1 is provided with fifth sliding channel 10 for said protruding rib 36 (see FIGS. 2 and 5). The matching of fifth sliding channel 10 and protruding rib 36 provides for the sliding connection of blade holder 1 inside blade shield 3. The said handle 4 is provided with sixth sliding channel 49 for said protruding rib 36 (see FIGS. 10 and 11) and when the handle 4 is inserted into the blade assembly, the matching of sixth sliding channel 49 and protruding rib 36 provides for the sliding connection of handle 4 inside blade shield 3.

Figure 12:
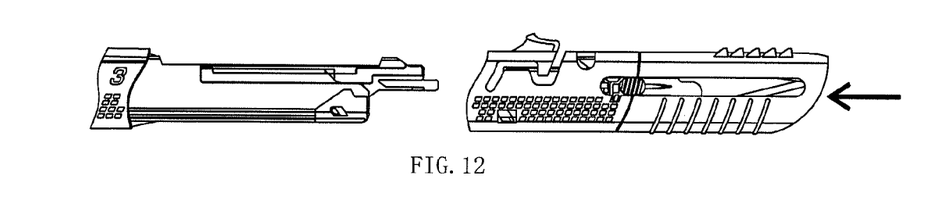
FIG. 12 through 17 illustrate the operation process of safety scalpel of embodiment 1 of the present invention.

The operation procedure of the safety scalpel of embodiment 1 is described as follows with accompanying drawings:

FIG. 12 shows the separation of handle 4 and the blade assembly before use of the scalpel. Wherein, the blade assembly consists of blade 2, blade holder 1 and blade shield 3. The blade 2 is fixed in the front portion of blade holder 1 and blade shield 3 is slidably mounted onto blade holder 1 and blade 2. In such a state, the blade 2 is arranged in blade shield 3 and the matching of first locking protrusion 13 of blade holder 1 and rear indent 35 of blade shield 3 locks the blade 2 in a closing state with respect to blade shield 3. Meanwhile, the first protrusion 321 of blade shield 3 is located in the first front locking channel 11 of blade holder 1, which also locks the blade holder 1 and blade 2 in a locking state with respect to blade shield 3 for increased safety. In such a state, the protrusion block 172 at the end of flexible arm 17 of blade holder 1 faces the clearance opening 37 of blade shield 3. The blade holder 1 is provided with an indent at position A (see FIG. 2) and the indent may be colored. The indent at position A may be seen from window 38 of blade shield 3 in the initial state.

Figure 13:
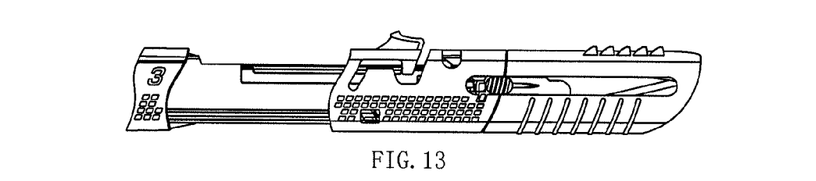

FIG. 13 shows the connection of scalpel handle 4 and the blade assembly. When the front of handle 4 is inserted into the blade assembly to be connected with blade holder 1, the second inclined block 44 of handle 4 acts on locking block 171 at the end of flexible arm 17 of blade holder 1 to force the flexible arm 17 to be flexed and force the protrusion block 172 to extend into clearance opening 37 with sideward movement. After the second inclined block 44 travels across the locking block 171, the flexible arm 17 automatically returns to its initial position resiliently and the second inclined block 44 engages the locking block 171 to connect the handle 4 and blade holder 1; When handle 4 and blade holder 1 are connected, the lower indent 45 of handle 4 travels across the upper protrusion 18 of blade holder 1 for engagement for more reliable connection of handle 4 and blade holder 1. After the handle 4 is connected with blade holder 1, the third locking protrusion 46 provided at the front end of handle 4 acts on first inclined block 15 set on blade holder 1 to force second flexible cantilever 140 of blade holder 1 to be flexed, so that first locking protrusion 13 of blade holder 1 leaves its original position to be unable to engage rear indent 35. Thus the locking of third locking protrusion 13 of blade holder 1 and rear indent 35 of blade shield 3 is released. After the handle 4 is connected with blade holder 1, the first sliding channel 12 at the back side of blade holder 1 and third sliding channel 41 set at the back side of handle 4 are abutted and the second protrusion 322 of blade shield 3 has been inserted into second front locking channel 47 on the front side of handle 4.

Figure 14:
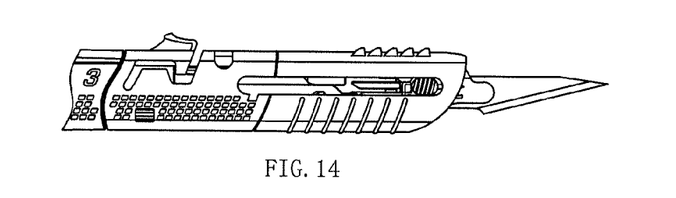

FIG. 14 shows the operation state after connection of scalpel handle 4 and blade assembly and opening of blade 2. The process of opening blade 2 is: in the state as shown in FIG. 13, when top unlocking button 31 is pressed, top unlocking button 31 forces first protrusion 321 to move from first front locking channel 11 at the back side to first sliding channel 12 and forces second protrusion 322 to move from second front locking channel 47 at the front side to fourth sliding channel 43. Then the blade shield 3 may be moved backward and during movement, the first protrusion 321 at the back side moves along first sliding channel 12 to third sliding channel 41 and second protrusion 322 at the front side moves backward along fourth sliding channel 43 until the first protrusion 321 at the back side falls into first rear locking channel 42 and the second protrusion 322 at the front side falls into second rear locking channel 48 to enter a locking state when the blade 2 is opened. Thus, the scalpel can be used for surgery.

Figure 15:
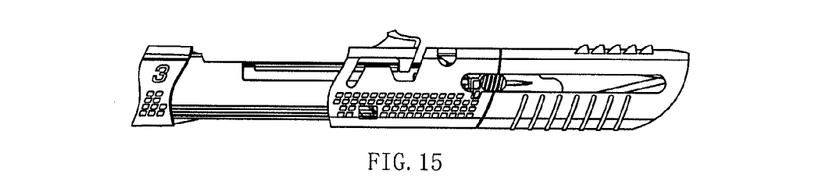

FIG. 15 shows the protection state of closing blade 2 after use of the scalpel. The process of closing blade 2 is: in the state as shown in FIG. 14, when top unlocking button 31 is pressed, top unlocking button 31 forces first protrusion 321 at the back side to move from first rear locking channel 42 to fall into third sliding channel 41 and forces second protrusion 322 at the front side to move from second rear locking channel 48 to fall into fourth sliding channel 43. Then the blade shield 3 may be moved forward until the first protrusion 321 at the back side falls into first front locking channel 11 and the second protrusion 322 at the front side falls into second front locking channel 47 to enter a locking state when the blade 2 is closed.

Figure 16:
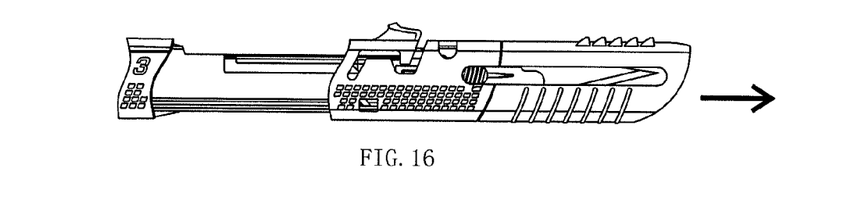

FIG. 16 shows the deadlocking state after use of the scalpel. The process is: in the state as shown in FIG. 15, continue moving the blade shield 3 forward and the first protrusion 321 at the back side travels from first front locking channel 11 over the inclined surface across locking block 16 to fall into deadlock channel 19. As the side of locking block 16 adjacent to deadlock channel 19 is a vertical surface, which forms the barrier, the first protrusion 321 cannot move backwards and it enters a permanent deadlocking state.

Figure 17:
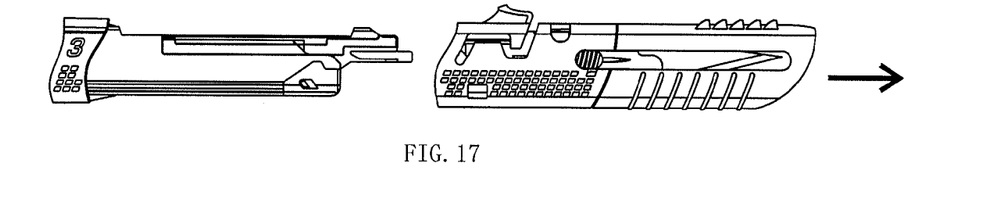

FIG. 17 shows the state of pulling handle 4 out of the blade assembly after use of the scalpel. The process is: in the state as shown in FIG. 16, to pull the handle 4 out of the blade assembly is to separate the handle 4 and blade assembly. It shall be noted that: after removal of handle 4, the blade assembly is in a deadlocking state and cannot be reused. In such a state, the protrusion block 172 misaligns with the clearance opening 37 and the handle 4 cannot be inserted into the blade assembly to be connected with blade holder 1 as the protrusion block 172 cannot make sideward movement through clearance opening 37. Thus the blade assembly cannot be inserted into handle 4 for re-use.

Additionally, if the process of entering the deadlocking state after use of scalpel as shown in FIG. 16 is omitted, it's possible to have the final effect as explained in FIG. 17 only by pulling out the handle 4. The reason is: during removal of the handle, the second inclined block 44 draws the blade holder 1 backward with respect to blade shield 3 through locking block 171 to force the first protrusion 321 to travel across locking block 16 to fall into deadlock channel 19 to enter a deadlocking state and force the protrusion block 172 to misalign with the clearance opening 37. In such a state, the handle 4 cannot be inserted into the blade assembly to be connected with blade holder 1 as the protrusion block 172 cannot make sideward movement through clearance opening 37.

Embodiment 2

A Kind of Safety Scalpel with Integral Connection Structure of Blade Holder and Handle The safety scalpel consists of blade shield 3, blade 2, blade holder 1 and handle 4, wherein the blade holder 1 is located in the front portion of handle 4, but the difference from embodiment 1 is that the blade holder 1 and handle 4 are of integral connection structure. The blade 2 is fixed in the front portion of blade holder 1 and blade shield 3 is slidably mounted on the blade holder 1. As the blade holder 1 and handle 4 of the present embodiment are of integral connection structure, they're usually made of plastics and they constitute, with blade shield 3 and blade 2, a disposable scalpel.

The following is a detailed description of blade shield 3, blade holder 1 and handle 4.

Referring to FIGS. 5 to 9, FIG. 18 and FIG. 9, the said blade shield 3 is provided with one top unlocking button 31 (see FIGS. 5 and 6) and top unlocking button 31 is the first flexible cantilever structure on the blade shield 3. The first flexible cantilever is provided with second locking protrusion 32 and second locking protrusion 32 includes a first protrusion 321 (see FIG. 6). The blade holder 1 is provided with first sliding channel 12 for first protrusion 321 correspondingly (see FIG. 19), and the first sliding channel 12 is arranged along the blade holder 1 with respect to the sliding direction of blade shield 3. The first sliding channel 12 is provided with first front locking channel 11 at its front end (see FIG. 19) and first front locking channel 11 is connected with the front end of first sliding channel 12. The deadlock channel 19 is set in front of first front locking channel 11 (see FIG. 19) and locking block 16 is set between deadlock channel 19 and first front locking channel 11 (see FIG. 19).

Figure 19:
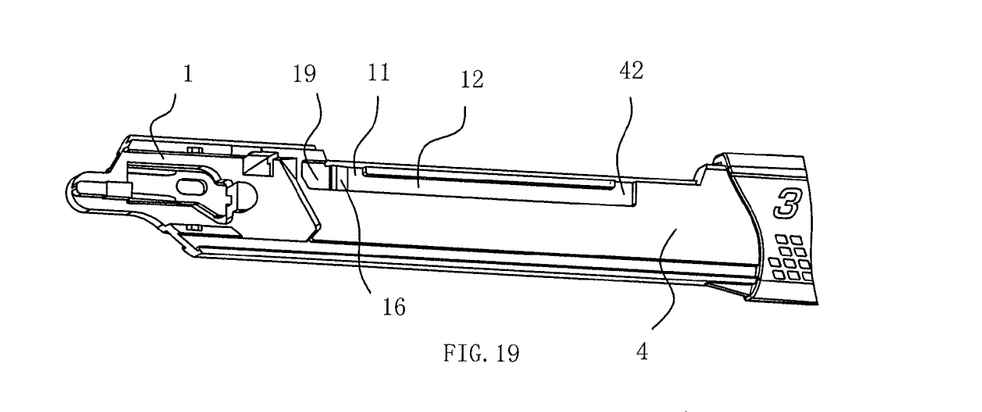
FIG. 19 is the back view illustrating the blade holder and handle of safety scalpel of embodiment 2 of the present invention.

During the operation process of the scalpel, the first protrusion 321 forms the following different states when it mates with first front locking channel 11, first sliding channel 12 and deadlock channel 19 respectively:

a. When first protrusion 321 is located in first front locking channel 11, the blade 2 is arranged inside blade shield 3 and the blade holder 1 and blade 2 are in a locking state with respect to blade shield 3;

b. When top unlocking button 31 is pressed, top unlocking button 31 forces first protrusion 321 to move from first front locking channel 11 to first sliding channel 12 and in such a state, the blade shield 3 is allowed to move with respect to blade holder 1 and blade 2;

c. When first protrusion 321 travels from first front locking channel 11 across the locking block 16 to fall into the deadlock channel 19, the blade 2 is arranged inside blade shield 3 and the blade holder 1 and blade 2 are in a deadlocking state with respect to blade shield 3;

In order to make blade holder 1 and blade shield 3 of the blade assembly smoothly transit from the locking state to the deadlocking state (see FIG. 19), the side of said locking block 16 adjacent to first front locking channel 11 is an inclined surface and the side of locking block 16 adjacent to deadlock channel 19 is a vertical surface.

In order to effectively control the opening and closing operation of blade 2 with respect to blade shield 3 and the locking in an opening or closing state, the first sliding channel 12 of said blade holder 1 extends backward along the length of handle. The first sliding channel 12 is provided with first rear locking channel 42 at the rear end (see. FIG. 19) and the first rear locking channel 42 is connected with the rear end of first sliding channel 12. When first protrusion 321 is located in first rear locking channel 42, the blade 2 extends out of blade shield 3 and blade holder 1 and blade 2 are in a locking state with respect to blade shield 3. The scalpel may be used for surgery in this state.

Figure 18:
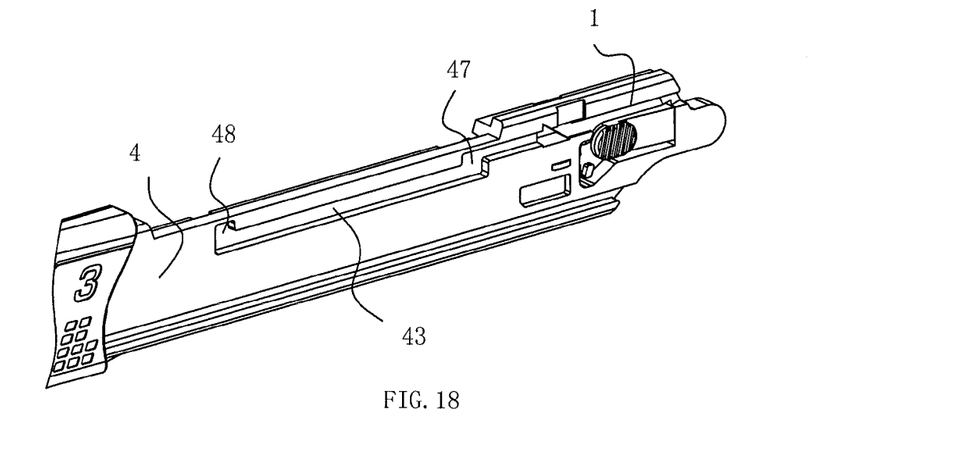
FIG. 18 is the front view illustrating the blade holder and handle of safety scalpel of embodiment 2 of the present invention.

The said first sliding channel 12, first front locking channel 11 and first rear locking channel 42 are set on one lateral face of blade holder 1 and handle 4, and fourth sliding channel 43 is set on the opposite lateral face of blade holder 1 and handle 4 at the corresponding position to first sliding channel 12 (see FIG. 18). The fourth sliding channel 43 is provided with second front locking channel 47 at its front end (see FIG. 18), which (47) is connected with the front end of fourth sliding channel 43 and fourth sliding channel 43 is provided with second rear locking channel 48 at its rear end (see FIG. 18), which is connected with the rear end of fourth sliding channel 43. The positions of second front locking channel 47 and first front locking channel 11 are corresponding and the positions of second rear locking channel 48 and first rear locking channel 42 are corresponding. The said second locking protrusion 32 includes second protrusion 322 (see FIG. 6), which is used to work with the fourth sliding channel 43, second front locking channel 47 and second rear locking channel 48.

The operation procedure of safety scalpel of embodiment 2 is described as follows (not shown in drawings):

1. Initial state before use.

The state is as shown in FIG. 13 of embodiment 1. In such a state, the blade 2 is arranged in blade shield 3. The first protrusion 321 at the back side of blade shield 3 is located in the first front locking channel 11 at the front end of first sliding channel 12, and the second protrusion 322 at the front side of blade shield 3 is located in the second front locking channel 47 at the front end of fourth sliding channel 43 and the blade holder 1 and blade 2 are in a locking state with respect to blade shield 3. The blade holder 1 is provided with an indent at position A (see FIG. 2) and the indent may be colored. The indent at position A may be seen from window 38 of blade shield 3 in the initial state.

2. Opening blade shield state before use

The state is as shown in FIG. 14 of embodiment 1. The process of opening blade 2 is: when top unlocking button 31 is pressed, top unlocking button 31 forces first protrusion 321 to move from first front locking channel 11 at the back side to first sliding channel 12 and forces second protrusion 322 to move from second front locking channel 47 at the front side to fourth sliding channel 43. Then the blade shield 3 may be moved backward and during movement, the first protrusion 321 at the back side moves backward along first sliding channel 12 and second protrusion 322 at the front side moves backward along fourth sliding channel 43 until the first protrusion 321 at the back side falls into first rear locking channel 42 and the second protrusion 322 at the front side falls into second rear locking channel 48 to enter a locking state when the blade 2 is opened. Thus, the scalpel may be used for surgery.

3. Closing the blade to be in a protection state after use of the scalpel

The state is as shown in FIG. 15 of embodiment 1. The process of closing blade 2 is: when top unlocking button 31 is pressed, top unlocking button 31 forces first protrusion 321 at the back side to move from first rear locking channel 42 to fall into first sliding channel 12 and forces second protrusion 322 at the front side to move from second rear locking channel 48 to fall into fourth sliding channel 43. Then the blade shield 3 may be moved forward until the first protrusion 321 at the back side falls into first front locking channel 11 and the second protrusion 322 at the front side falls into second front locking channel 47 to enter a locking state when the blade 2 is closed.

4. Enter the deadlocking state after use of the scalpel.

The state is as shown in FIG. 16 of embodiment 1. The process is: continue moving the blade shield 3 forwards and the first protrusion 321 at the back side travels from first front locking channel 11 over the inclined surface across locking block 16 to fall into deadlock channel 19. As the side of locking block 16 adjacent to deadlock channel 19 is a vertical surface, which forms the barrier, the first protrusion 321 cannot move backward and it enters the permanent deadlocking state.

It should be noted that the above described embodiments are only for illustration of technical concept and characteristics of the present invention with the purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A safety scalpel consisting of:
a blade shield;
a blade;
a blade holder; and
a handle, the blade holder being located in a front portion of the handle, the blade holder and the handle being of a separate plug-together type connection structure, and the blade being fixed in a front portion of the blade holder, the blade shield being slidably mounted onto the blade holder, wherein:
the blade shield is provided with a top unlocking button forming a first flexible cantilever on the blade shield, the first flexible cantilever being provided with a second locking protrusion including a first protrusion, the blade holder is provided with a first sliding channel for receiving the first protrusion, the first sliding channel being arranged along the blade holder in a sliding direction of the blade shield when slidably mounted onto the blade holder,
the first sliding channel is provided with a first front locking channel positioned at a front end of the first sliding channel, a deadlock channel of the blade holder is positioned in front of the first front locking channel, and a first locking block of the blade holder is positioned between the deadlock channel and the first front locking channel, and
the first protrusion is configured to mate with the first front locking channel, the first sliding channel, and the deadlock channel, respectively, such that during an operation process of the scalpel:
  a. when the first protrusion is positioned in the first front locking channel, the blade is arranged inside the blade shield, and the blade holder and the blade are in a locking state with respect to the blade shield,
  b. when the top unlocking button is pressed, the top unlocking button forces the first protrusion to move from the first front locking channel to another portion of the first sliding channel such that the blade shield is unlocked and free to move with respect to the blade holder and the blade, and
  c. when the first protrusion is moved from the first front locking channel across the first locking block to fall into the deadlock channel, the blade is arranged inside the blade shield, and the blade holder and the blade are in a deadlocking state with respect to the blade shield, wherein
the blade holder is provided with a flexible arm at its rear end which extends backward, the flexible arm is provided with a second locking block and a protrusion block, the protrusion block extends toward an inner wall of the blade shield, the inner wall of the blade shield is provided with a clearance opening for receiving the protrusion block, and the handle is provided with a second inclined block in the front portion of the handle, such that the first protrusion is located in the first front locking channel and the protrusion block faces the clearance opening in an initial assembled state,
when the handle is inserted into the blade holder for connection, the second inclined block acts on the second locking block to force the flexible arm to be flexed and force the protrusion block to extend into the clearance opening with a sideward movement,
after the second inclined block travels across the second locking block, the flexible arm automatically returns to its initial position resiliently and the second inclined block engages the second locking block to connect the handle and blade holder, and
during removal of the handle, the second inclined block draws the blade holder backward with respect to the blade shield through the second locking block to force the first protrusion to travel across the first locking block to fall into the deadlock channel and force the protrusion block to misalign with the clearance opening, such that the handle is prevented from being re-inserted into the blade holder for connection as the protrusion block is prevented from making the sideward movement through the clearance opening.

2. The safety scalpel of claim 1, wherein
a first side of the first locking block adjacent to the first front locking channel is an inclined surface, and a second side of the first locking block adjacent to the deadlock channel is a vertical surface.

3. The safety scalpel of claim 2, wherein the blade holder is provided with a second flexible cantilever, one side of the second flexible cantilever being provided with a first locking protrusion, a lateral unlocking button, and a first inclined block, a side of the blade shield is provided with a second sliding channel for receiving the lateral unlocking button to position the lateral unlocking button inside the second sliding channel, the second sliding channel being provided with a front indent at its front end and a rear indent at its rear end, the first locking protrusion mates with the front indent to lock the blade in an open state with respect to the blade shield, and the first locking protrusion mates with the rear indent to lock the blade in a closed state with respect to the blade shield, the lateral unlocking button, upon being pressed, is configured to release a mating state of the first locking protrusion with the front indent or a mating state of the first locking protrusion with the rear indent, the first inclined block is configured to mate with a third locking protrusion positioned at a front end of the handle, and in a state in which the handle is connected with the blade holder, the third locking protrusion acts on the first inclined block to force the second flexible cantilever to be flexed, so that the first locking protrusion leaves its original position and is prevented from engaging the front indent or the rear indent, and when the handle is disconnected from the blade holder, the third locking protrusion is separated from the first inclined block, the second flexible cantilever automatically returns to its initial position resiliently and returns the first locking protrusion to its initial position, so that the first locking protrusion engages the front indent or the rear indent.

4. The safety scalpel of claim 1, wherein the handle is provided with a third sliding channel arranged to connect with the first sliding channel such that, when the handle and the blade holder are connected, the third sliding channel and the first sliding channel are abutted, so that the first protrusion can slide along the first sliding channel to the third sliding channel, and the third sliding channel is provided with a first rear locking channel positioned at a rear end of the third sliding channel, such that when the first protrusion is located in the first rear locking channel, the blade extends out of the blade shield, and the blade holder and the blade are in a locking state with respect to the blade shield.

5. The safety scalpel of claim 4, wherein the first sliding channel and the first front locking channel are set on a first lateral face of the blade holder, the third sliding channel and the first rear locking channel are set on a first lateral face of the handle, a fourth sliding channel is set on a second, opposite lateral face of the handle at a position corresponding to the first sliding channel and the third sliding channel, the fourth sliding channel being provided with a second front locking channel positioned at a front end of the fourth sliding channel, and the fourth sliding channel being provided with a second rear locking channel positioned at a rear end of the fourth sliding channel, wherein positions of the second front locking channel and the first front locking channel correspond to each other, and positions of the second rear locking channel and the first rear locking channel correspond to each other, and the second locking protrusion includes a second protrusion configured to engage with the fourth sliding channel, the second front locking channel, and the second rear locking channel.

6. The safety scalpel of claim 1, wherein the blade holder is provided with an upper protrusion, and the handle is provided with a lower indent configured to engage with the upper protrusion in a state in which the handle and the blade holder are connected.

7. The safety scalpel of claim 1, wherein the blade shield is provided with a protruding rib extending along the blade holder in the sliding direction of the blade shield, and the blade holder is provided with a fifth sliding channel for receiving the protruding rib, the mating of the fifth sliding channel with the protruding rib providing for a sliding connection of the blade holder inside the blade shield, and the handle is provided with a sixth sliding channel for receiving the protruding rib, the mating of the sixth sliding channel with the protruding rib providing for the sliding connection of the handle inside the blade shield when the handle is inserted into the blade holder.

* * * * *